(12) United States Patent
Locke et al.

(10) Patent No.: US 11,344,664 B2
(45) Date of Patent: May 31, 2022

(54) AMBULATORY THERAPY SYSTEM INCORPORATING ACTIVITY AND ENVIRONMENTAL SENSING CAPABILITY

(71) Applicant: KCI Licensing, Inc., San Antonio, TX (US)

(72) Inventors: Christopher Brian Locke, Bournemouth (GB); James A. Luckemeyer, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 343 days.

(21) Appl. No.: 15/760,176

(22) PCT Filed: Nov. 1, 2016

(86) PCT No.: PCT/US2016/059847
§ 371 (c)(1),
(2) Date: Mar. 14, 2018

(87) PCT Pub. No.: WO2017/087157
PCT Pub. Date: May 26, 2017

(65) Prior Publication Data
US 2018/0250452 A1    Sep. 6, 2018

Related U.S. Application Data

(60) Provisional application No. 62/256,391, filed on Nov. 17, 2015.

(51) Int. Cl.
*A61M 1/00* (2006.01)
*A61B 5/11* (2006.01)
(Continued)

(52) U.S. Cl.
CPC ............ *A61M 1/90* (2021.05); *A61B 5/1118* (2013.01); *A61B 5/4833* (2013.01); *A61B 5/746* (2013.01);
(Continued)

(58) Field of Classification Search
CPC .................. A61B 5/746; A61B 5/1118; A61B 2562/0219; A61M 1/0025
See application file for complete search history.

(56) References Cited

U.S. PATENT DOCUMENTS 1,355,846 A  10/1920 Rannells
2,547,758 A  4/1951 Keeling
(Continued)

FOREIGN PATENT DOCUMENTS

AU  550575 B2  3/1986
AU  745271 B2  3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Catharine L Anderson
*Assistant Examiner* — Arjuna P Chatrathi

(57) ABSTRACT

A system for providing therapy to a tissue site is described. The system can include a light sensor, a motion sensor, and a controller. The controller can be communicatively coupled to the source of negative pressure, the light sensor, and the motion sensor. In some embodiments, the controller can be configured to receive a first signal from the light sensor indicative of ambient light, receive a second signal from the
(Continued)

motion sensor indicative of activity, and activate alert based on the first signal and the second signal.

67 Claims, 4 Drawing Sheets

(51) Int. Cl.
    *A61B 5/00* (2006.01)
    *G16H 20/30* (2018.01)

(52) U.S. Cl.
    CPC ...... *G16H 20/30* (2018.01); *A61B 2560/0242* (2013.01); *A61B 2562/0219* (2013.01); *A61M 2205/056* (2013.01); *A61M 2205/332* (2013.01); *A61M 2205/3306* (2013.01); *A61M 2230/63* (2013.01)

(56) References Cited

U.S. PATENT DOCUMENTS

| | | | |
|---|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,366,692 B2 * | 2/2013 | Weston ................. A61M 1/90 604/319 |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2005/0171410 A1 * | 8/2005 | Hjelt ................. G16H 40/67 600/300 |
| 2008/0071216 A1 * | 3/2008 | Locke ................. A61M 5/1415 604/119 |
| 2009/0292264 A1 | 11/2009 | Hudspeth et al. |
| 2012/0253485 A1 | 10/2012 | Weast et al. |
| 2013/0296816 A1 * | 11/2013 | Greener ............ A61M 1/0003 604/320 |
| 2013/0304006 A1 | 11/2013 | Toth |

(56) References Cited

U.S. PATENT DOCUMENTS

| | | | |
|---|---|---|---|
| 2014/0163491 A1 | 6/2014 | Schuessler et al. | |
| 2014/0215246 A1* | 7/2014 | Lee | A61B 5/02055 713/323 |
| 2015/0080788 A1 | 3/2015 | Blott et al. | |

FOREIGN PATENT DOCUMENTS

| | | | |
|---|---|---|---|
| AU | 755496 B2 | 12/2002 | |
| CA | 2005436 A1 | 6/1990 | |
| DE | 26 40 413 A1 | 3/1978 | |
| DE | 43 06 478 A1 | 9/1994 | |
| DE | 29 504 378 U1 | 9/1995 | |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2 195 255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/020041 A1 | 9/1994 | |
| WO | 96/05873 A1 | 2/1996 | |
| WO | 97/18007 A1 | 5/1997 | |
| WO | 99/13793 A1 | 3/1999 | |
| WO | 2009089390 A3 | 11/2009 | |
| WO | 2012091975 A1 | 7/2012 | |
| WO | 2014120832 A1 | 8/2014 | |
| WO | WO-2014120832 A1 * | 8/2014 | A61B 5/02055 |
| WO | 2015/094724 A1 | 6/2015 | |
| WO | WO-2015103556 A1 * | 7/2015 | A61B 5/1118 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634 639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sept. 3, 1997.

Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain—Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

(56) References Cited

OTHER PUBLICATIONS

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

ISR and Written Opinion for corresponding PCT/US2016/059847 dated Jan. 17, 2017.

Australian Examination Report for Corresponding Application No. 2016357216, dated Nov. 2, 2020.

Japanese Notice of Rejection for Corresponding Application No. 2018-524834, dated Sep. 29, 2020.

\* cited by examiner

AMBULATORY THERAPY SYSTEM INCORPORATING ACTIVITY AND ENVIRONMENTAL SENSING CAPABILITY

RELATED APPLICATION

This application is the National Stage of International Application No. PCT/US2016/059847, entitled "Ambulatory Therapy System Incorporating Activity and Environmental Sensing Capability," filed Nov. 1, 2016 and claims the benefit of U.S. Provisional Patent Application No. 62/256,391, entitled "Ambulatory Therapy System Incorporating Activity and Environmental Sensing Capability," filed Nov. 17, 2015, all of which are incorporated herein by reference for all purposes.

TECHNICAL FIELD

The invention set forth in the appended claims relates generally to tissue treatment systems and more particularly, but without limitation, to a system for capturing movement and environmental data for therapy modification.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of reduced-pressure therapy are widely known, improvements to reduced-pressure systems, components, and processes may benefit healthcare providers and patients.

BRIEF SUMMARY

New and useful systems, apparatuses, and methods for monitor and adjust therapy for a tissues site are set forth in the appended claims. Illustrative embodiments are also provided to enable a person skilled in the art to make and use the claimed subject matter.

For example, in some embodiments, a system for providing therapy to a tissue site is described. The system can include a light sensor, a motion sensor, and a controller. The controller can be communicatively coupled to the source of negative pressure, the light sensor, and the motion sensor. In some embodiments, the controller can be configured to receive a first signal from the light sensor indicative of ambient light, receive a second signal from the motion sensor indicative of activity, and activate an alert based on the first signal and the second signal.

More generally, a system for providing negative-pressure therapy is described. The system can include a tissue interface configured to be positioned adjacent a tissue site and a sealing member configured to be positioned over the tissue interface to form a sealed space. A negative-pressure source can be configured to be fluidly coupled to the sealed space. The system can also include a light sensor, a motion sensor, and a controller communicatively coupled to the negative-pressure source, the light sensor, and the motion sensor. In some embodiments, the controller can be configured to receive a signal from the light sensor and a signal from the motion sensor, actuate the source of negative pressure, and modify an operating parameter of the negative-pressure source in response to the signal from the light sensor and the signal from the motion sensor.

Alternatively, other example embodiments may include a method for providing negative-pressure therapy. The method can provide a therapy system having a light sensor, a motion sensor, and a controller. The controller may be communicatively coupled to the light sensor and the motion sensor. In some embodiments, the controller can be configured to receive input from the light sensor and the motion sensor, and conduct ambulatory therapy in response to the input. The motion sensor may be coupled to a patient, and a prescribed number of activity periods may be received. Signals received from the light sensor and the motion sensor may be monitored, and in response to the signals received from the light sensor and the motion sensor, the patient may be prompted to engage in ambulation.

Another method for providing negative-pressure therapy is also described. A therapy system can be provided. The therapy system may include a light sensor, a motion sensor, and a controller communicatively coupled to the light sensor and the motion sensor. The controller can be configured to receive input from the light sensor and the motion sensor, and adjust operating parameters of negative-pressure therapy in response to the input. The motion sensor can be coupled to a patient, and a prescribed number of activity periods can be received by the controller. The controller can monitor signals received from the light sensor and the motion sensor, and in response to the signals received from the light sensor and the motion sensor, determine whether to enter a sleep mode. If the sleep mode is entered, the controller can adjust operating parameters of negative-pressure therapy to operate in a sleep mode. If the sleep mode is not entered, the controller can adjust operating parameter of negative-pressure therapy to operate in a normal mode.

An apparatus for managing therapeutic activity of a patient is also described. The apparatus can include a light sensor configured to provide a light signal indicative of ambient light, an activity sensor configured to provide an activity signal indicative of the patient's activity, and a controller coupled to the light sensor and to the motion sensor. The controller can be configured to compare the light signal to a light threshold, compare the activity signal to an activity threshold, and determine a number of activity intervals based on the activity signal. The controller can also be configured to prompt the patient to increase activity if the light signal is greater than the light threshold, the activity signal is less than the activity threshold, and the number of activity intervals is less than a target number.

An apparatus for providing negative-pressure therapy is described. The apparatus can include a negative-pressure source, a light sensor configured to provide a light signal indicative of ambient light, and an activity sensor configured to provide an activity signal indicative of the patient's activity. A controller can be coupled to the negative-pressure source, to the light sensor, and to the motion sensor. In some embodiments, the controller can be configured to: compare the light signal to a light threshold, compare the activity signal to an activity threshold, and modify an operating parameter if the light signal is less than the light threshold and the activity signal is less than the activity threshold.

In another embodiment, a method for providing negative-pressure therapy is described. A therapy system is provided and includes: a light sensor; a motion sensor; a user interface; and a controller communicatively coupled to the light sensor and the motion sensor. The controller may be configured to receive input from the light sensor and the motion sensor, and adjust operating parameters of negative-pressure therapy in response to the input. An active mode and a sleep mode of the therapy system can be set with the user interface. Signals received from the light sensor and the motion sensor can be monitored. In response to the signals received from the light sensor and the motion sensor, whether to enter the sleep mode can be determined. If the sleep mode is entered, operating parameters of negative-pressure therapy can be adjusted to operate in the sleep mode. If the sleep mode is not entered, operating parameter of negative-pressure therapy can be adjusted to operate in the active mode.

In another embodiment, a method for providing negative-pressure therapy is described. A therapy system is provided and includes: a light sensor; a motion sensor; a user interface; and a controller communicatively coupled to the light sensor and the motion sensor. The controller may be configured to receive input from the light sensor and the motion sensor, and adjust operating parameters of negative-pressure therapy in response to the input. An active mode and a sleep mode of the therapy system can be set with the user interface. Signals received from the light sensor and the motion sensor can be monitored, and the signals received from the light sensor and the motion sensor can be transmitted to a remote server.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The example embodiments may be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
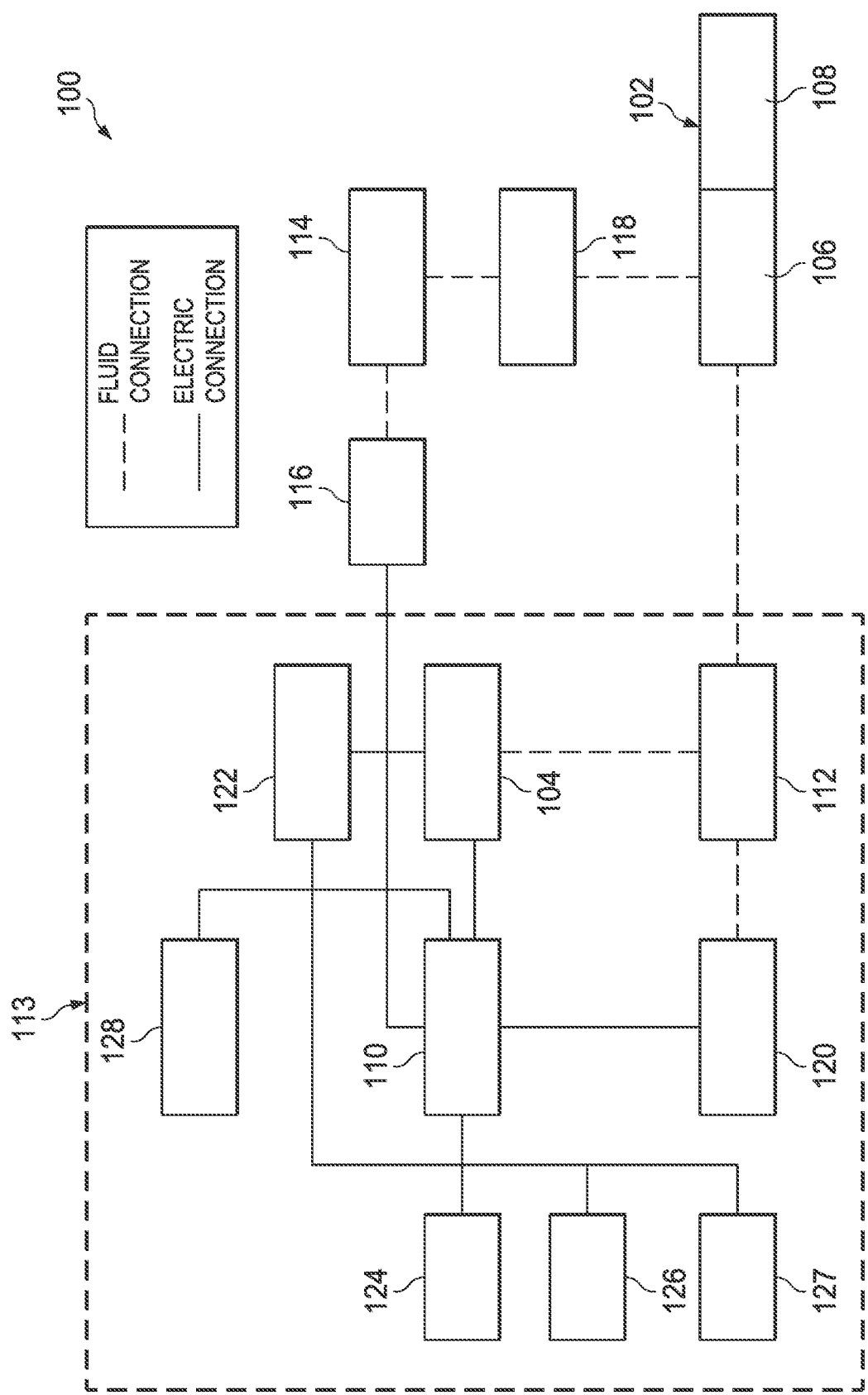
FIG. 1 is a functional block diagram of an example embodiment of a therapy system that can provide negative-pressure therapy and instillation therapy in accordance with this specification.

FIG. 1 is a simplified functional block diagram of an example embodiment of a therapy system 100 that can provide negative-pressure therapy and instillation therapy in accordance with this specification.

The term "tissue site" in the context of the described embodiments broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of tissue that are not necessarily wounded or defective, but are instead areas in which it may be desirable to add or promote the growth of additional tissue. For example, negative pressure may be applied to a tissue site to grow additional tissue that may be harvested and transplanted.

The therapy system 100 may include a negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a tissue interface 108. A regulator or a controller, such as a controller 110, may also be coupled to the negative-pressure source 104.

In some embodiments, a dressing interface may facilitate coupling the negative-pressure source 104 to the dressing 102. For example, a dressing interface may be a T.R.A.C.® Pad or Sensa T.R.A.C.® Pad available from Kinetic Concepts, Inc. (KCI) of San Antonio, Tex. The therapy system 100 may optionally include a fluid container, such as a container 112, coupled to the dressing 102 and to the negative-pressure source 104.

The therapy system 100 could also include a source of instillation solution. For example, a solution source 114 may be fluidly coupled to the dressing 102, as illustrated in the example embodiment of FIG. 1. The solution source 114 may be fluidly coupled to a positive-pressure source such as a positive-pressure source 116 in some embodiments, or may be fluidly coupled to the negative-pressure source 104.

A regulator, such as an instillation regulator 118, may also be fluidly coupled to the solution source 114 and the dressing 102. In some embodiments, the instillation regulator 118 may also be fluidly coupled to the negative-pressure source 104 through the dressing 102, as illustrated in the example of FIG. 1.

Additionally, the therapy system 100 may include sensors to measure operating parameters and provide feedback signals to the controller 110 indicative of the operating parameters. As illustrated in FIG. 1, for example, the therapy system 100 may include a pressure sensor 120, an electric sensor 122 configured to detect voltage and/or current changes, an activity sensor or motion sensor, such as an accelerometer 124, a light sensor 126, and/or a time-of-day chip 127. These sensors may be coupled to the controller 110. The pressure sensor 120 may also be coupled or configured to be coupled to a distribution component and to the negative-pressure source 104. The electric sensor 122 may also be coupled to the negative-pressure source 104 or the solution source 114. The accelerometer 124 may be coupled to the controller 110 and configured to provide an activity signal indicative of a patient's activity. Similarly, the light sensor 126 may be coupled to the controller 110 and configured to provide a light signal indicative of ambient light in the external environment. The therapy system 100 may also include a user interface 128 coupled to the controller 110. In some embodiments, the negative-pressure source 104, the controller 110, the container 112, the pressure sensor 120, the electric sensor 122, the accelerometer 124, the light sensor 126, and the time-of-day chip 127 may be components of a therapy device 113.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be directly or indirectly coupled to other components. For example, the negative-pressure source 104 may be directly coupled to the controller 110, and may be indirectly coupled to the dressing 102 through the container 112.

The fluid mechanics of using a negative-pressure source to reduce pressure in another component or location, such as within a sealed therapeutic environment, can be mathematically complex. However, the basic principles of fluid mechanics applicable to negative-pressure therapy and instillation therapy are generally well-known to those skilled in the art. The process of reducing pressure may be described illustratively herein as "delivering," "distributing," or "generating" negative pressure, for example. Similarly, the process of instilling fluid may be described illustratively herein as "delivering," "distributing," or "generating" fluid, for example.

In general, exudates and other fluids flow toward lower pressure along a fluid path. Thus, the term "downstream" typically implies a position in a fluid path relatively closer to a source of negative pressure or further away from a source of positive pressure. Conversely, the term "upstream" implies a position relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit, such as the therapy device 113. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may be a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

The average pore size of a foam may vary according to needs of a prescribed therapy. For example, in some embodiments, the tissue interface 108 may be a foam having pore sizes in a range of about 400 microns to about 600 microns. The tensile strength of the tissue interface 108 may also vary according to needs of a prescribed therapy. For example, the tensile strength of a foam may be increased for instillation of topical treatment solutions. In one non-limiting example, the tissue interface 108 may be an open-cell, reticulated polyurethane foam such as GranuFoam® dressing or Vera-Flo® foam, both available from Kinetic Concepts, Inc. of San Antonio, Tex.

The tissue interface 108 may be either hydrophobic or hydrophilic. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 108 may further serve as a scaffold for new cell-growth, or a scaffold material may be used in conjunction with the tissue interface 108 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least about 300 $g/m^2$ per twenty-four hours in some embodiments. In some example embodiments, the cover 106 may be a polymer drape, such as a polyurethane film, that is permeable to water vapor but impermeable to liquid. Such drapes typically have a thickness in the range of about 25 microns to about 50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between about 25 grams per square meter (gsm) and about 65 gsm. Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy. In some embodiments, the container 112 may be a component, such as an absorbent component of a dressing, configured to be positioned adjacent to the tissue site or tissue interface to store liquids.

The solution source 114 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment or sealed space proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

In addition to negative-pressure therapy and instillation therapy, ambulation may aid in healing of a tissue site. Ambulation may move fluids around the body, reduce edema, and encourage normal biological function and well-being. As a result, patients may be encouraged to engage in ambulatory activities as part of the therapy process. Unfortunately, patients may find ambulation difficult while using typical therapy devices. The size of negative-pressure therapy and instillation systems may make it difficult for a patient to move, or may forget that ambulation is required or fail to understand the level of activity necessary to receive therapeutic benefits. In addition, the light and noise of some therapy devices may compromise patient rest, prompting a patient to disable or remove the therapy device while sleeping. Often, removal of the therapy device can lead to negative patient outcomes.

The therapy system 100 can overcome these problems and others by prompting a patient to engage in ambulatory therapy at an intensity level. In some embodiments, the therapy system 100 can measure a patient's activity and environmental conditions. In some embodiments, sensors may be deployed in a therapy device that is worn by a patient. Additionally or alternatively, sensors may be deployed in a separate monitoring unit, which can be carried or worn by a patient. The monitoring unit may be communicatively coupled to a therapy device that is providing negative-pressure therapy and/or instillation therapy. In some embodiments, the sensors may use standard or proprietary protocols that can communicate wirelessly with the controller 110 or other microprocessor.

Data from the sensors can also be recorded, which may be particularly advantageous for improving quality of life and compliance for ambulatory patients. For example, the therapy system 100 may be portable or otherwise mobile, allowing an ambulatory patient to resume many daily activities while undergoing therapy, which can prevent or reduce edema. In some embodiments, the controller 110 can process data from a sensor such as the accelerometer 124 to analyze patient activity data and modify operating parameters or alarms based on the patient activity data to reduce interference with the patient activity. For example, the controller 110 may use data from the accelerometer 124 to identify rest periods and, in response, change therapy pressure, alarm thresholds, volume levels, and backlight levels of the therapy device 113. Generally, a therapy pressure may be a desired pressure in a sealed therapeutic environment for optimal treatment of a tissue site based on the desired treatment outcomes. Often, the therapy pressure may be about −125 mm Hg. Additionally or alternatively, the controller 110 may provide reports indicative of compliance based on patient activity, such as the number of steps taken by a patient and the number of rest periods. The controller 110 may also provide reports of impacts to both the patient and the device that can be used by the manufacturer to service the therapy device.

Figure 2:
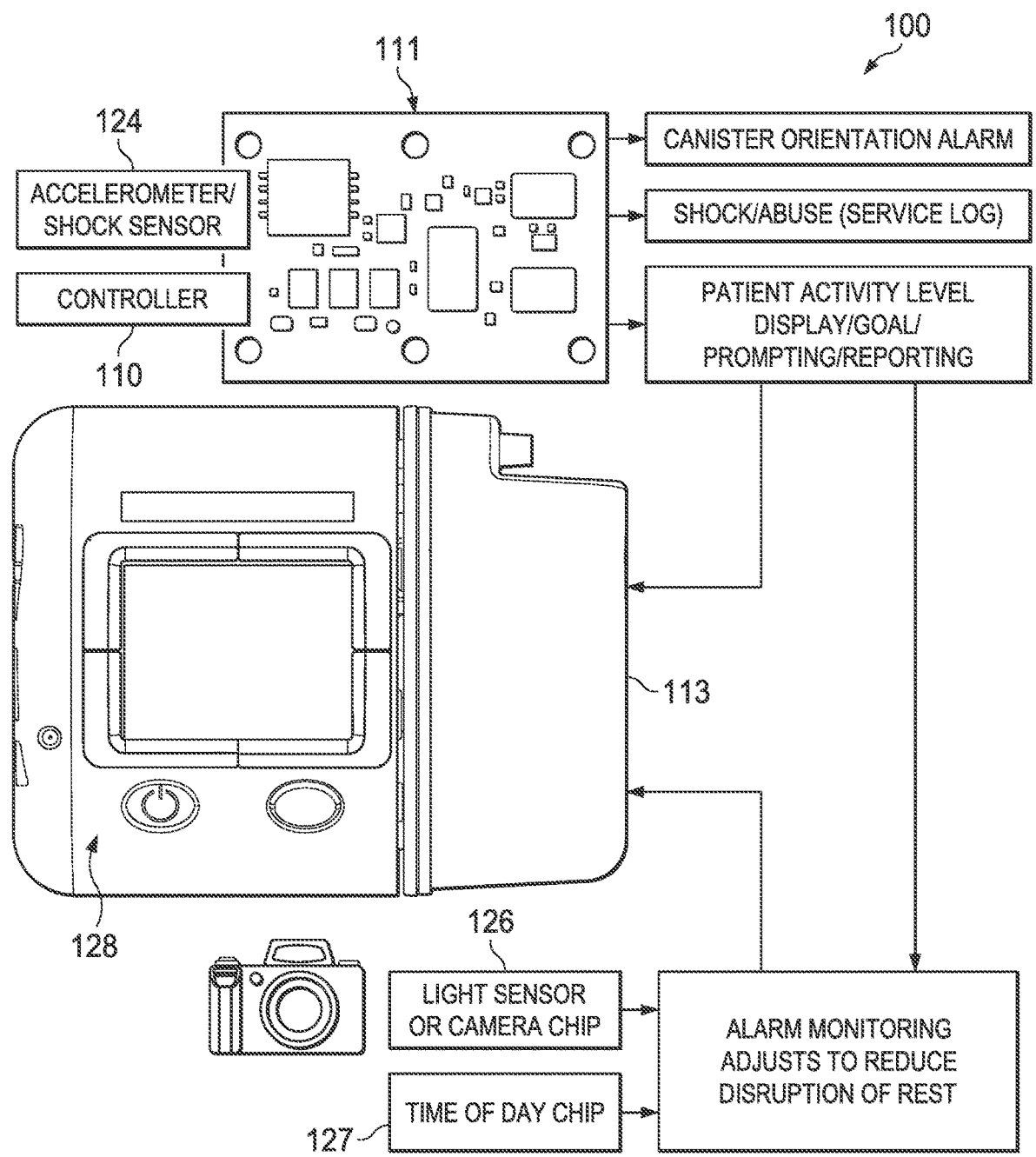
FIG. 2 is a schematic diagram illustrating additional details of system-level operations of the therapy system of FIG. 1.

FIG. 2 is a schematic diagram illustrating system level functions that may be associated with some embodiments of the therapy system 100. As illustrated in the example of FIG. 2, the accelerometer 124 and other sensors can be deployed on a controller board 111 associated with the controller 110 to measure orientation, detect free-fall, monitor shock and vibration, provide a motion-activated operator interface, or any combination thereof to collect patient activity data. The controller board 111 may be disposed in the therapy device 113 in some embodiments. The therapy device 113 may also include the negative-pressure source 104, the electric sensor 122, the container 112, the pressure sensor 120, and the user interface 128. In some embodiments, the therapy device 113 may include the light sensor 126 and the time-of-day chip 127. The time-of-day chip 127 may be configured to determine a time of day and a passage of set time intervals. Using the accelerometer 124, the therapy system 100 may provide a canister orientation alarm if the container 112 is in an orientation that may disrupt therapy. The therapy system 100 can also record a service log of instances of shock or abuse to the therapy device 113 based upon signals from the accelerometer 124. The therapy system 100 can also provide information, prompts, alarms and other alerts. For example, the controller 110 may display patient activity level or goals through the user interface 128, prompt a patient to engage in prescribed activity, report the number of patient activity intervals, and engage in remote monitoring of patient activity. The therapy system 100 can also provide alarm monitoring and alarm adjustment to reduce the disruption of patient rest using the light sensor 126 and the time-of-day chip 127.

A controller, such as the controller 110, may be a microprocessor or computer that is programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, alarm thresholds, backlighting, or sound levels, for example. The controller 110 is also preferably configured to receive one or more input signals, such as a feedback signal, and programmed to modify one or more operating parameters based on the input signals.

A controller may also be a computing device or system, such as a programmable logic controller, or a data processing system, for example. In some embodiments, a controller may be configured to receive input from one or more devices, such as a user interface, a sensor, or a flow meter, for example. In some embodiments, a controller may receive input, such as an electrical signal, from an alternative source, such as through an electrical port, for example.

A programmable logic controller (PLC) may be a digital computer configured to receive one or more inputs and send one or more outputs in response to the one or more inputs. A PLC may include a non-volatile memory configured to store programs or operational instructions. In some embodiments, the non-volatile memory may be operationally coupled to a battery-back up so that the non-volatile memory retains the programs or operational instructions if the PLC otherwise loses power. In some embodiments, a PLC may be configured to receive discrete signals and continuous signals and produce discrete and continuous signals in response.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code in order to reduce the number of times code is retrieved from bulk storage during execution.

A user interface, such as the user interface 128, may be a device configured to allow communication between a controller and an environment external to a therapy device. In some embodiments, an external environment may include an operator or a computer system configured to interface with a therapy device, for example. In some embodiments, a user interface may receive a signal from a controller and present the signal in a manner that may be understood by an external environment. In some embodiments, a user interface may receive signals from an external environment and, in response, send signals to a controller.

In some embodiments, a user interface may be a graphical user interface, a touchscreen, or one or more motion tracking devices. A user interface may also include one or more display screens, such as a liquid crystal display ("LCD"), lighting devices, such as light emitting diodes ("LED") of various colors, and audible indicators, such as a whistle, configured to emit a sound that may be heard by an operator. A user interface may further include one or more devices, such as knobs, buttons, keyboards, remotes, touchscreens, ports that may be configured to receive a discrete or continuous signal from another device, or other similar devices; these devices may be configured to permit the external environment to interact with the user interface. A user interface may permit an external environment to select a therapy to be performed with a therapy device. In some embodiments, a user interface may display information for an external environment such as a duration of therapy, a type of therapy, an amount of negative pressure being supplied, an amount of instillation solution being provided, a fluid level of a container, or a fluid level of a cartridge, for example.

The controller 110 may be communicatively coupled to components of the therapy system 100, such as a valve, a flow meter, a sensor, a user interface, or a pump, for example, to control operation of the same. As used herein, communicative coupling may refer to a coupling between components that permits the transmission of signals between the components. In some embodiments, the signals may be discrete or continuous signals. A discrete signal may be a signal representing a value at a particular instance in a time period. A plurality of discrete signals may be used to represent a changing value over a time period. A continuous signal may be a signal that provides a value for each instance in a time period. The signals may also be analog signals or digital signals. An analog signal may be a continuous signal that includes a time varying feature that represents another time varying quantity. A digital signal may be a signal composed of a sequence of discrete values.

In some embodiments, communicative coupling may include transmission of signals through wireless mechanisms. For example, the user interface 128 may be a remotely located device, and the controller 110 may communicate with the user interface 128 using wireless communication. Wireless communication can include radio communication, microwave communication, free-space optical communication, sonic communication, and electromagnetic induction, for example.

In some embodiments, communicative coupling between a controller and other devices may be one-way communication. In one-way communication, signals may only be sent in one direction. For example, a sensor may generate a signal that may be communicated to a controller, but the controller may not be capable of sending a signal to the sensor. In some embodiments, communicative coupling between a controller and another device may be two-way communication. In two-way communication, signals may be sent in both directions. For example, a controller and a user interface may be communicatively coupled so that the controller may send and receive signals from the user interface. Similarly, a user interface may send and receive signals from a controller. In some embodiments, signal transmission between a controller and another device may be referred to as the controller operating the device. For example, interaction between a controller and a valve may be referred to as the controller: operating the valve; placing the valve in an open position, a closed position, or a metering position; and opening the valve, closing the valve, or metering the valve.

Sensors, such as the pressure sensor 120, the electric sensor 122, the accelerometer 124, the light sensor 126, and the time-of-day chip 127 can be apparatuses operable to detect or measure a physical phenomenon or property, and generally provide a signal indicative of the phenomenon or property that is detected or measured. For example, the pressure sensor 120 and the electric sensor 122 may be configured to measure one or more operating parameters of the therapy system 100, such as changes in the voltage or current used by the negative-pressure source 104. In some embodiments, the pressure sensor 120 may be a transducer configured to measure pressure in a pneumatic pathway and convert the measurement to a signal indicative of the pressure measured. In some embodiments, for example, the pressure sensor 120 may be a piezoresistive strain gauge. The electric sensor 122 may optionally measure operating parameters of the negative-pressure source 104, such as the voltage or current, in some embodiments. Preferably, the signals from the pressure sensor 120 and the electric sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

In other embodiments, the therapy system 100 may include a sensor configured to respond to an auditory input, such as a microphone. A microphone may be a transducer configured to convert sound into an electrical or optical signal. A microphone may be configured to provide a signal to the controller 110. In some embodiments, the signal from a microphone may be processed as an ambient environment noise, and the controller 110 may determine based on the signal from the microphone whether the patient is in the active mode or in the sleep mode. The therapy system 100 may also use a microphone to exit the sleep mode based on an ambient noise level without requiring a command from a user or clinician. In other embodiments, the controller 110 may include speech recognition software, and a microphone may be provided with the therapy system 100 to permit the use of voice commands from a user or clinician. For example, a patient may speak a command such as "sleep mode" to place the therapy system 100 into the sleep mode.

The therapy system 100 may also include an electroacoustic transducer or speaker. The controller 110 may communicate with the speaker to produce sound understandable by a user or clinician. For example, the controller 110 may provide an electrical audio signal to produce an alarm tone, speech, or other sound to indicate a status of the therapy system 100. The controller 110 may also provide a signal that can be produced as speech to provide status of the therapy system or encouragement to the user. For example, if a user follows a protocol, the controller 110 may provide a spoken phrase, such as "your activity level today has been good" to the user through the speaker. In some embodiments, the therapy system 100 is monitored from a remote location. If the therapy system 100 is monitored from a remote location, wireless communication may permit a clinician monitoring the therapy system 100 to communicate with the user through a speaker and to receive communication from the user through the microphone. In still other embodiments, the therapy system 100 may include storage media capable of receiving data representative of an auditory message, store the data, and replay the data at a predetermined time or in response to a predetermined signal.

In some example embodiments, the accelerometer 124 may be a 3-axis accelerometer, such as the MMA8653FC from Freescale Semiconductor, Inc. The exemplary accelerometer may have a low-profile 2×2×1.0 mm dual-flat no-leads package with high sensitivity of 1 micro g per least significant bit, low noise: 150 micro g per root Hertz that is independent of resolution, a 7 micro amps low-power mode, a 1.62 to 3.6V interrupt and inter-integrated circuit interface supply, and an output data rate of about 1.5 to 800 Hz. The accelerometer 124 may sense 3 axes of motion and both positive and negative loads between about 2 g and about 8 g. The accelerometer 124 may detect orientation, free-fall, activity, shock/vibration, and user interface motion controls. In some embodiments, the accelerometer 124 may determine a number of steps taken and a cadence of the steps taken. In some embodiments, the accelerometer 124 may be worn by a person to detect an orientation of the person, i.e., standing, sitting, or laying down. The light sensor 126, such as a photosensor, camera, or other photo sensitive device, may also be deployed to detect or measure light in some embodiments. The light sensor 126 can detect electromagnetic energy and, in response, generate a signal corresponding to the intensity of the electromagnetic energy.

In some embodiments, the accelerometer 124 and the light sensor 126 may be built into a device that is worn by the patient and may be physically coupled to the therapy device 113. In other embodiments, the accelerometer 124 and the light sensor 126 may be a separate device that can communicate, wired or wirelessly, with the controller 110. In still other embodiments, the accelerometer 124 and the light sensor 126 may be incorporated into a third-party device and the therapy device 113 may be configured to control or receive information from the third-party activity monitor using proprietary or standardized protocols.

Figure 3:
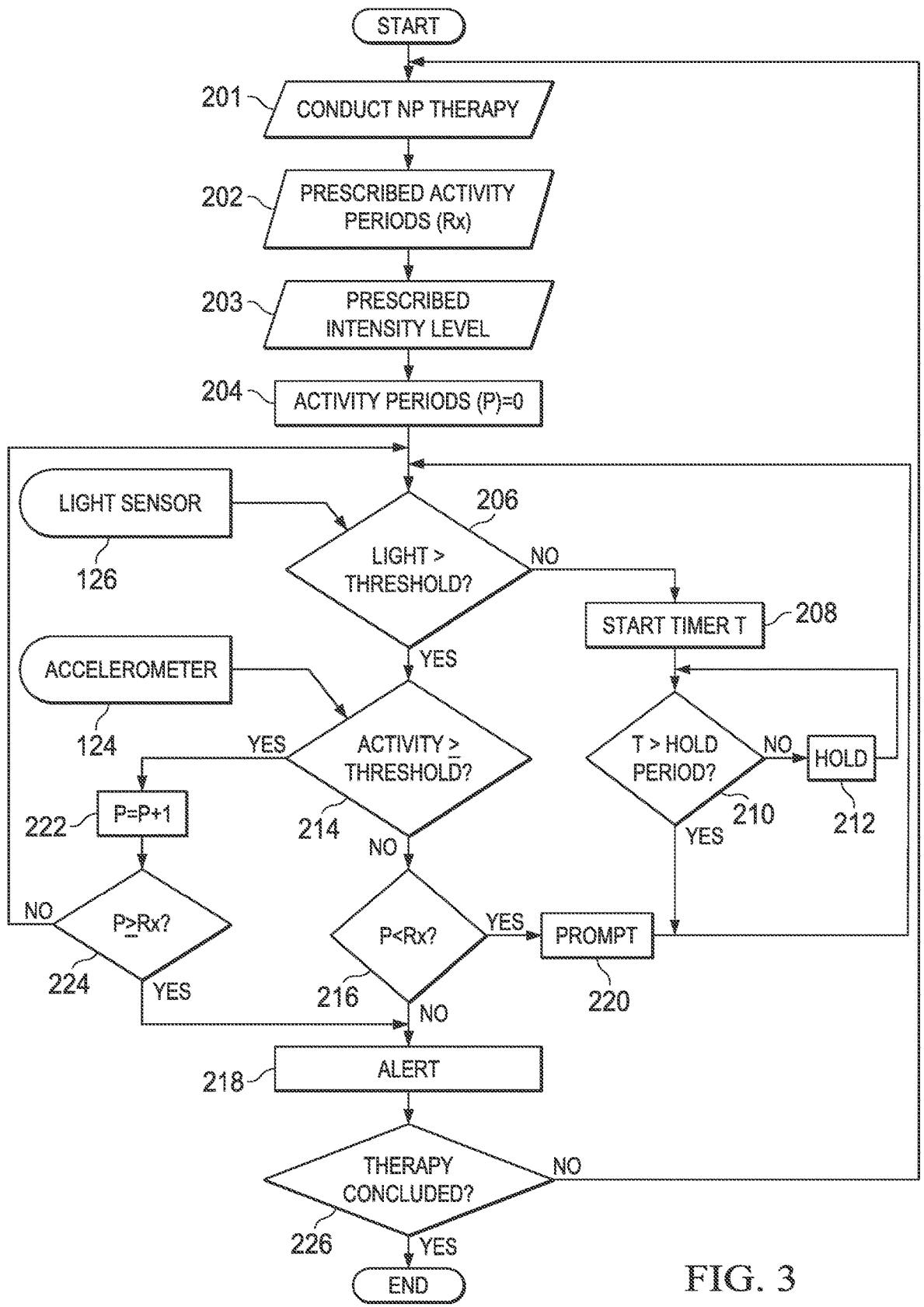
FIG. 3 is a flow chart illustrating additional details that may be associated with an example embodiment of an operation of the therapy system of FIG. 1.

FIG. 3 is a flow diagram illustrating additional details that may be associated with the operation of some example embodiments of the therapy system 100. In general, FIG. 3 is illustrative of operations that can be implemented in a controller, such as the controller 110, to monitor patient compliance with prescribed activity periods and prompt the patient to encourage compliance with ambulatory therapy. Ambulatory therapy may include prescribed intervals or periods of activity, a prescribed activity intensity, and/or accumulated activity over a period of time, for example, accumulated activity over a period of twenty-four hours. Ambulatory therapy may include walking or other types of therapeutic activity, and may be engaged in by a patient while undergoing negative-pressure therapy, instillation therapy, or both negative-pressure therapy and instillation therapy.

A target number of activity intervals can be selected or otherwise configured in the controller 110. For example, a target number of activity intervals in a period may be prescribed by a clinician. The target number of activity intervals may be entered into or otherwise configurable by the controller 110. For example, a clinician may prescribe and enter 4 activity intervals for a twenty-four hour period into the therapy device 113 through the user interface 128. The data entered may be stored by the controller 110 and used to control operation of the therapy device 113.

An activity intensity may also be selected or otherwise configured in some embodiments of the controller 110. For example, a clinician may prescribe activity having a low intensity level, a medium intensity level, or a high intensity level. Data from sensors such as the accelerometer 124 may be analyzed by the controller 110 to monitor or measure intensity of activity. For example, distance, duration, and speed of movement can be monitored or measured to evaluate compliance with a prescribed intensity. A clinician may select an intensity level based on the clinical judgment of the clinician. For example, a clinician may consider the overall health of the patient to determine how much activity the patient can reasonably engage in and how different activity levels may impact healing of the tissue site. In some embodiments, low intensity activity may include covering a distance of less than about 10 feet, a speed of about 1 mile per hour, and a duration of about 10 minutes. Medium intensity activity may include covering a distance of between about 10 feet and about 30 feet, a speed of about 1 mile per hour to about 2 miles per hour, and a duration of about 10 minutes to about 20 minutes. High intensity activity may include covering a distance of between about 30 feet and about 50 feet, a speed of about 2 miles per hour to about 4 miles per hour and a duration of about 20 minutes to about 40 minutes. In some embodiments, a prescribed activity intensity level can be selected or entered into the user interface 128 of the therapy device 113. For example, the clinician can enter a low intensity activity level into the therapy device 113. The data entered may be stored by the controller 110 and used to control operation of the therapy device 113. In some embodiments, tiered activity intervals may be entered into or otherwise configurable by the controller 110. For example, a user may select a first activity interval at a first activity intensity, a second activity interval at a second intensity, and a third activity interval at a third intensity, where the active intensity of the first, second, and third activity intensities may increase, decrease, vary, or stay the same between activity intervals. In some embodiments, the therapy system 100 may include biosensors, such as a heart rate monitor, a blood oxygen sensor, and/or a respiratory rate sensor. The therapy system 100 may also receive signals from the heart rate monitor, the blood oxygen sensor, and/or a respiratory rate sensor to determine the level of the patient's activity.

In some embodiments, negative-pressure therapy may be provided at block 201. For example, the controller 110 can operate the negative-pressure source 104 and receive signals from the pressure sensor 120 and the electric sensor 122 to provide negative-pressure therapy to a tissue site through the dressing 102.

The controller 110 can also manage ambulatory therapy. In some embodiments, the controller 110 may manage ambulatory therapy without negative-pressure therapy or intermittent with negative-pressure therapy. In still other embodiments, the controller 110 can additionally or alternatively provide instillation therapy. In some embodiments, the controller 110 can manage ambulatory therapy with negative-pressure therapy. For example, as illustrated in FIG. 3, a prescribed number of activity intervals (Rx) can be entered or otherwise configured at block 202. For example, the controller 110 may receive a prescribed number of intervals through user interface 128. A prescribed activity intensity level may also be set or otherwise configured at block 203. For example, a default intensity level may be configured in the controller 110, an operator may select a level from a menu, or may enter the intensity level at a prompt. A counter for a number of completed activity intervals (P) can be initialized at block 204. For example, the controller 110 sets a storage location for P to zero.

At block 206, a light intensity can be compared to a light threshold, such as a sleep threshold intensity. For example, the controller 110 can receive an input from the light sensor 126 indicative of light in the patient's environment. In some embodiments, a light signal may be a measurement of the luminous flux in the ambient environment and can be valued in lumens. If the light intensity is not greater than the threshold, the process can continue along the NO path to block 208. For example, if the controller 110 determines that the signal from the light sensor 126 does not exceed the sleep threshold intensity, the process continues to block 208. At block 208, the process can set a time value (T) to zero and start a timer. For example, the controller 110 can set a timer to 0 and start operation of the timer. At block 210, the process can determine if a current time T is greater than a hold period. A hold period may be a period of time where the controller 110 maintains the operation of the system 100 in its current operating state. If the current time T is not greater than the hold period, the process follows the NO path to block 212. At block 212, the process holds for a hold period. For example, the controller 110 can wait to take any further action for a predetermined hold period of 30 minutes. At block 210, if the current time T is greater than the hold period, the process follows the YES path to block 206. Blocks 208, 210, and 212 may collectively be referred to as a hold loop or a hold routine. Blocks 208, 210, and 212 may pause the therapy system 100 for a predetermined hold period, for example, one hour.

At block 206, if the light intensity is greater than the light threshold, the process follows the YES path to block 214. At block 214, a signal from an activity sensor, such as the accelerometer 124, can be compared to an activity threshold. For example, the controller 110 may receive signals from the accelerometer 124 indicative of distance, speed, and duration of movement. In some embodiments, the accelerometer 124 may measure acceleration and deceleration in micro g in each of three orthogonal directions. The measured acceleration and deceleration may be used by the controller 110 to determine a distance traveled, a speed of the travel, and how long the travel took. If the current level of activity is not greater than or equal to the activity threshold, the process continues on the NO path to block 216. At block 216, the number of completed activity intervals is compared to the prescribed number of activity intervals. For example, the controller 110 can compare the value of $R_x$ to the value of P. If the number of completed activity intervals P is greater than or equal to the prescribed activity intervals $R_x$, the user can be alerted at block 218. For example, the controller 110 may actuate a visual or auditory alert to indicate that the user is engaging in more physical activity than prescribed. After alerting the user at block 218, the process can determine if therapy is concluded at block 226. For example, the controller 110 can determine if ambulatory therapy and negative-pressure therapy have concluded. If ambulatory therapy and negative-pressure therapy have not concluded, the process can repeat by conducting negative-pressure therapy at block 201. If ambulatory therapy and negative-pressure therapy have concluded, the process can terminate.

If the total number of activity periods P is less than the prescribed number of activity periods $R_x$, the process follows the YES path to an activity loop. At block 220, for example, the user can be prompted to engage in activity. In some embodiments, a prompt may be a visual and/or auditory message activated by the controller 110 on the user interface 128. The process returns to block 206, completing the activity loop.

At block 214, if the activity is greater than or equal to the activity threshold, the process can enter an alert loop, and the number of completed activity intervals can be incremented at block 222. For example, the controller 110 can add 1 to an activity counter, such as the total number of completed activity intervals P. At block 224, the number of completed activity intervals P for a period can be compared to a target number of activity intervals, such as the prescribed activity intervals R. For example, the controller 110 can compare the value of P to the value of R. If P is less than $R_x$, the process follows the NO path, returning to block 206. If the number of activity intervals P is greater than or equal to the prescribed activity intervals $R_x$, the user can be alerted at block 218. For example, the controller 110 may actuate the user interface 128 to provide a visual or auditory alert to indicate that the user is engaging in more physical activity than prescribed, ending the alert loop.

After alerting the user at block 218, the process can determine if therapy is concluded at block 226. For example, the controller 110 can determine if ambulatory therapy and negative-pressure therapy have concluded. If ambulatory therapy and negative-pressure therapy have not concluded, the process can repeat by conducting negative-pressure therapy at block 201. If ambulatory therapy and negative-pressure therapy have concluded, the process can terminate.

Figure 4:
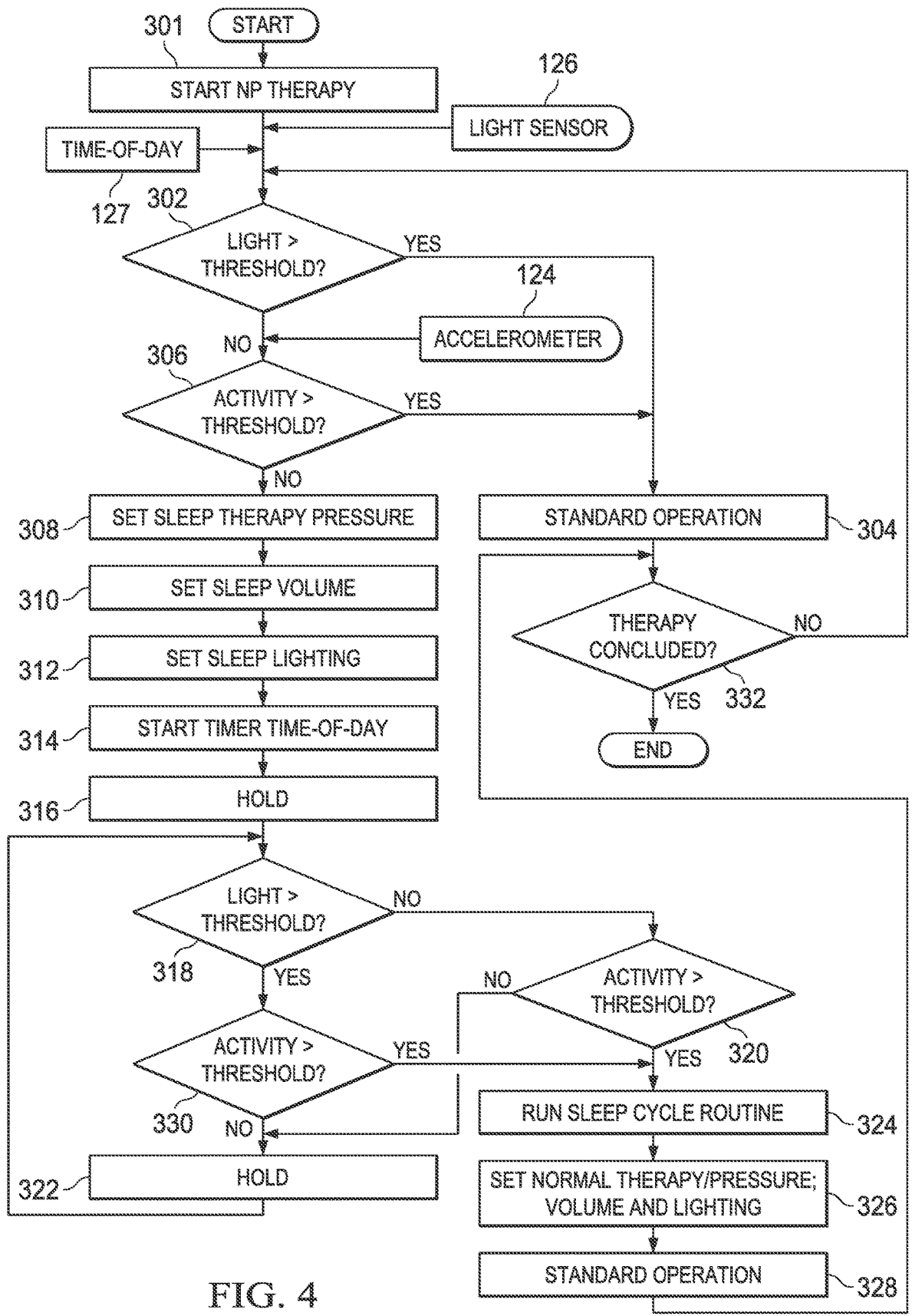
FIG. 4 is a flow chart illustrating additional details that may be associated with an example embodiment of another operation of the therapy system of FIG. 1.

FIG. 4 is a flow diagram illustrating additional details that may be associated with the operation of some example embodiments of the therapy system 100. In general, FIG. 4 is illustrative of operations that can be implemented in some embodiments of the controller 110 to modify operating parameters based on activity and environment data. In some embodiments, the controller 110 can activate a sleep mode based on data from an activity sensor, a light sensor, and a time-of-day chip. For example, a sleep mode may be activated if a signal from an activity sensor is below an activity threshold, a signal from a light sensor is below a light threshold, and a time-of-day chip indicates a normal resting period. A sleep mode may also be activated if a signal from an activity sensor is below an activity threshold and a signal from a light sensor is below a light threshold. A sleep mode can include changes to the therapy protocol, alarm thresholds, volume levels, and backlight levels, for example. In some embodiments, the controller 110 may lower the therapy pressure in a sleep mode if a large leak is detected. For example, a therapy pressure may be about 125 mm Hg, but if a large leak is detected in a sleep mode, the therapy system 100 can lower the therapy pressure to 75 mm Hg so that the leak can be managed at a lower pump duty without setting off an alarm, and the patient is not disturbed. The lower therapy pressure may be referred to as a sleep therapy pressure. If data from the sensors indicates changed conditions, such as an activity signal that exceeds a threshold or a light signal that exceeds a threshold, the controller 110 may restore an active mode. In an active mode, the pressure can be restored to the prescribed therapy pressure and an alert regarding the leak can be reported. In some embodiments, sleep modes can be programmed or learned, and alarms can be adjusted or delayed until the device determines that the patient is awake. For example, if a leak or blockage is detected an hour before normal wake-up time, the therapy system 100 can disable therapy and wait the hour before alerting.

Referring to FIG. 4 for illustration, negative-pressure therapy may be started at block 301. For example, the controller 110 can operate the negative-pressure source 104 and receive signals from the pressure sensor 120 and the electric sensor 122 to provide negative-pressure therapy to the tissue site through the dressing 102. During the process, the controller 110 may receive input from the time-of-day chip 127, allowing the process to monitor the passage of periods of time during the operations performed herein. At block 302, input from the light sensor 126 can be compared to a light threshold. For example, the controller 110 can compare the signal from the light sensor 126 to a sleep threshold intensity, which can be indicative of a sleep environment. The sleep threshold intensity may vary by patient; generally, a room lit by a light source emitting less than 200 lumens may be indicative of a sleep environment. If the light intensity is greater than the light threshold, a standard or active mode can be started or maintained at block 304. For example, the controller 110 may operate the therapy system 100 in a standard or active mode to provide negative-pressure therapy and/or instillation therapy at prescribed therapy levels while monitoring patient activity as described with respect to FIG. 3.

At block 302, if the light intensity is less than or equal to the light threshold, input from an activity sensor can be compared to an activity threshold. For example, the controller 110 may receive a signal from the accelerometer 124, which can be indicative of the patient's current activity level. In some embodiments, the activity threshold may be set or otherwise configured by the controller 110 to a value that is indicative of a patient who is sleeping. If an activity signal is greater than the activity threshold, the controller 110 can activate or continue operating a standard mode. For example, the controller 110 may operate the therapy system 100 to provide negative-pressure therapy and/or instillation therapy at prescribed therapy levels while monitoring patient activity as described with respect to FIG. 3. During standard mode operation, the process may determine if therapy is concluded at block 332. For example, the controller 110 can determine if ambulatory therapy and negative-pressure therapy have concluded. If ambulatory therapy and negative-pressure therapy have not concluded, the process can repeat by conducting negative-pressure therapy at block 301. If ambulatory therapy and negative-pressure therapy have concluded, the process can terminate.

At block 306, if an activity signal is less than an activity threshold, the controller 110 can enter a sleep mode at block 308. For example, the controller 110 may reduce therapy pressure in a sleep mode. A sleep volume may also be set in a sleep mode. For example, the controller 110 can adjust the volume of audible alarms of the therapy system 100 to one-half the volume of the audible alarms in an active mode. At block 312, system lighting can also be reduced. For example, the controller 110 can adjust the backlight of the user interface 128 and the intensity of any indicators or other devices of the therapy system 100 that emit light to one-half the normal operating intensity.

At block 316, the sleep mode can be held for a hold time. For example, the controller 110 may hold the sleep mode for a predetermined hold time period of 1 hour. At block 318, the process compares a light intensity to the light threshold. For example, the controller 110 receives a signal from the light sensor 126 indicative of the current light intensity of the patient's environment. The controller 110 then compares the light intensity received from the light sensor 126 to the light threshold. If the light intensity is less than or equal to the light threshold, the process follows the NO path to block 320. At block 320, the process determines if the activity intensity is greater than the activity threshold. For example, the controller 110 receives a signal from the accelerometer 124 that is indicative of the patient's current activity level. If the activity intensity is not greater than the activity threshold, the process follows the NO path to block 322. At block 322, the process holds for a hold time period, then returns to block 318.

At block 320, if the activity intensity is greater than the activity threshold, the process continues on the YES path to block 324. At block 324, the process operates a sleep cycle routine. For example, the controller 110 can operate a sleep cycle routine. A sleep cycle routine may be a logical routine operated by a computing device that can determine a sleep pattern of a user based on inputs from a light sensor, an activity sensor, and a timer. For example, the controller 110 can determine a sleep pattern of a patient using signals from the accelerometer 124, the light sensor 126, and the time of day chip 127. The sleep cycle routine can determine a time at which the patient generally appears to be awake, appears to be asleep, and how long the patient appears to remain asleep. At block 326, the process sets a normal therapy pressure, a normal volume, and a normal lighting. For example, the controller 110 sets the therapy pressure to 125 mm Hg for negative-pressure therapy, the volume for the therapy system to full volume, and the light intensity for the therapy system 100 to full intensity. At block 328, the process provides therapy under standard operating conditions. For example, the controller 110 may operate the therapy system 100 to provide negative-pressure therapy and/or instillation therapy at prescribed therapy levels while monitoring patient activity as described with respect to FIG. 3. During standard mode operation, the process may determine if therapy is concluded at block 332. For example, the controller 110 can determine if ambulatory therapy and negative-pressure therapy have concluded. If ambulatory therapy and negative-pressure therapy have not concluded, the process can repeat by conducting negative-pressure therapy at block 301. If ambulatory therapy and negative-pressure therapy have concluded, the process can terminate.

At block 318, if the light intensity exceeds the light threshold, the process continues on the YES path to block 330. At block 330, the process determines if the activity intensity is greater than the sleep threshold activity intensity. For example, the controller 110 receives a signal from the accelerometer 124 indicative of the patient's current activity and compares the signal to the activity threshold. If the activity intensity is less than or equal to the activity threshold, the process follows the NO path to block 322. At block 322, the process holds for a hold time period, then returns to block 318. At block 330, if the activity intensity is greater than the activity threshold, the process continues on the YES path to block 324 and follows the process described above.

In some embodiments, the system can detect orientation of the therapy device, allowing the therapy device to alert the user if the user has placed the therapy device in an un-favorable position or if the canister filter is blocked due to a tilt of a canister. In still other embodiments, the accelerometer 124 may be used to detect and log patterns of use, feedback regarding pump activation, user interface control, such as sensing with the device is placed face down, implying that display can be dimmed, and dead-reckoning estimates through temporary dead zones. In some embodiments, the controller 110 can record and report activity for compliance review.

In some embodiments, the total number of completed activity intervals P for a particular therapy period can be stored by the controller 110. The total number of completed activity intervals P for the particular time period may be accessed at a later time by a clinician or other user, for example, through the user interface 128, so that the data may be used to aid in diagnosis of the patient's condition and the appropriate treatment for the patient. For example, the data, including total number of completed activity intervals P, time-of-day information, activity intensity information, can be used to determine if a depressed patient got out of bed, or if the patient deviated from therapy or the patient's normal routine. The total number of sleep cycles may also be stored by the controller 110. The information can be accessed at a later time by a clinician or other user, for example, through the user interface 128, to determine whether a patient is getting sufficient sleep and whether the duration of the patient's sleep is sufficient to accumulate appropriate rapid eye movement ("REM") sleep.

The systems, apparatuses, and methods described herein may provide significant advantages. For example, a clinician can prescribe a program of mobility for a patient, who can be prompted to comply. The patient's activity can be recorded, providing the clinician with a report of activity and rest periods. Alarms and other user interfaces can be adapted based on signals from activity and environment sensors indicative of a patient sleeping or resting to reduce or minimize patient disruptions. The prescribed program can be reasserted when the patient is awake. In some embodiments, the system can provide alerts if the product is placed in an un-favorable position or has been dropped. The system can record data about impacts and any concerns that may need to be alerted to the manufacturer upon return or servicing. The device can also alert the patient if a very significant impact may have caused damage to the device and place the product in a safe mode where settings are restricted and pressure lowered. A sudden acceleration of the device may indicate that the patient has fallen; the device can alert a clinician, user, or provider to check the device if a sudden acceleration is detected. The device can reduce disruptions to daily activities and rest, while encouraging compliance with ambulatory therapy prescriptions. In systems including instillation therapy, the system can avoid or delay instillation therapy during determined sleeping periods.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for providing therapy to a tissue site, the system comprising:
   a light sensor;
   a motion sensor;
   a therapy unit including a source of negative pressure; and
   a controller communicatively coupled to the source of negative pressure, the light sensor, and the motion sensor, the controller configured to:
      receive a light signal from the light sensor indicative of ambient light,
      receive an activity signal from the motion sensor indicative of activity,
      activate an alert based on the light signal and the activity signal, and
      adjust an alert threshold based on the light signal and the activity signal.

2. The system of claim 1, wherein the controller is further configured to determine a number of activity intervals based on the activity signal.

3. The system of claim 2, wherein the alert is activated if the light signal is greater than a light threshold, the activity signal is less than an activity threshold, and the number of activity intervals is less than a target number.

4. The system of claim 2, wherein the alert is activated if the number of activity intervals is greater than a target number.

5. The system of claim 2, wherein:
   a first alert is activated if the light signal is greater than a light threshold, the activity signal is less than an activity threshold, and the number of activity intervals is less than a target number; and
   a second alert is activated if the number of activity intervals is greater than the target number.

6. The system of claim 1, further comprising a tissue interface configured to be positioned adjacent the tissue site.

7. The system of claim 6, further comprising a sealing member configured to be positioned over the tissue interface to form a sealed space.

8. The system of claim 6, further comprising the source of negative pressure configured to be fluidly coupled to the tissue interface, and the controller is configured to operate the source of negative pressure to deliver a therapy pressure to the tissue interface.

9. The system of claim 8, wherein the controller is further configured to modify an operating parameter based on the light signal and the activity signal.

10. The system of claim 9, wherein the controller is further configured to reduce the operating parameter if the light signal is less than a light threshold and the activity signal is less than an activity threshold.

11. The system of claim 9, wherein the operating parameter is the therapy pressure.

12. The system of claim 9, wherein the operating parameter is a light intensity or a sound intensity.

13. The system of claim 1, wherein the controller is further configured to receive an ambulatory therapy and determine if a user is complying with the ambulatory therapy based on the light signal and the activity signal.

14. The system of claim 1, wherein the light sensor is a photosensor.

15. The system of claim 1, wherein the light sensor is a camera.

16. The system of claim 1, wherein the motion sensor is an accelerometer.

17. The system of claim 1, wherein the therapy unit includes an active mode and a sleep mode.

18. The system of claim 17, wherein the therapy unit further comprises a user interface configured to receive a selection of the active mode or the sleep mode.

19. The system of claim 18, wherein the controller is configured to select the active mode and the sleep mode in response to the light signal and the activity signal.

20. A system for providing negative-pressure therapy, the system comprising:
   a tissue interface configured to be positioned adjacent a tissue site;
   a sealing member configured to be positioned over the tissue interface to form a sealed space;
   a negative-pressure source configured to be fluidly coupled to the sealed space;
   a light sensor;
   a motion sensor; and
   a controller communicatively coupled to the negative-pressure source, the light sensor, and the motion sensor, the controller configured to:
      receive a light signal from the light sensor and an activity signal from the motion sensor,
      actuate the source of negative pressure, and
      modify an operating parameter of the negative-pressure source in response to the light signal from the light sensor and the activity signal from the motion sensor.

21. The system of claim 20 wherein the operating parameter is a therapy pressure of the negative-pressure source.

22. The system of claim 20 wherein the operating parameter is a therapy pressure of the negative-pressure source, a light intensity, or a sound intensity.

23. The system of claim 20, wherein the light sensor is a photosensor.

24. The system of claim 20, wherein the light sensor is a camera.

25. The system of claim 20, wherein the motion sensor is an accelerometer.

26. The system of claim 20, wherein the controller is configured to adjust a therapy pressure to a sleep therapy pressure if the light signal from the light sensor is less than a light threshold and the activity signal from the motion sensor is less than an activity threshold.

27. The system of claim 20, wherein the controller is configured to adjust a light intensity of the system to a sleep intensity if the light signal from the light sensor is less than a light threshold and the activity signal from the motion sensor is less than an activity threshold.

28. The system of claim 20, wherein the controller is configured to adjust a volume of the system to a sleeping system volume if the light signal from the light sensor is less than a light threshold and the activity signal from the motion sensor is less than an activity threshold.

29. The system of claim 20, wherein if the light signal from the light sensor is less than a light threshold and the activity signal from the motion sensor is less than an activity threshold, the controller is further configured to:
   adjust a therapy pressure of the system to a sleep therapy pressure;
   adjust a light intensity of the system to a sleep threshold intensity; and
   adjust a volume of the system to a sleep system volume.

30. The system of claim 29, wherein the therapy pressure is about 125 mm Hg and the sleep therapy pressure is about 75 mm Hg.

31. The system of claim 29, wherein the sleep threshold intensity is about one-half the light intensity.

32. The system of claim 28, wherein the sleeping system volume of the system is about one-half of the volume.

33. The system of claim 26, wherein the controller is further configured to prompt a user to engage in ambulatory therapy for a prescribed number of therapy periods if the light signal from the light sensor is greater than the light threshold or the activity signal from the motion sensor is greater than the activity threshold.

34. The system of claim 26, wherein the controller is further configured to prompt a user to engage in ambulatory therapy for a prescribed number of therapy periods if the light signal from the light sensor is greater than the light threshold and the activity signal from the motion sensor is greater than the activity threshold.

35. A method for providing negative-pressure therapy, the method comprising:
   providing a therapy system having:
      a light sensor;
      a motion sensor;
      a controller communicatively coupled to the light sensor and the motion sensor, the controller configured to receive light input from the light sensor and activity input from the motion sensor, and conduct ambulatory therapy in response to the light input and the activity input;
   coupling the motion sensor to a patient;
   receiving a prescribed number of activity periods;
   monitoring signals received from the light sensor and the motion sensor; and
   in response to the signals received from the light sensor and the motion sensor, prompting the patient to engage in ambulation.

36. The method of claim 35, wherein the light sensor is a photosensor.

37. The method of claim 35, wherein the light sensor is a camera.

38. The method of claim 35, wherein the motion sensor is an accelerometer.

39. The method of claim 35, further comprising positioning a dressing adjacent to a tissue site of the patient.

40. The method of claim 39, further comprising fluidly coupling a negative-pressure source to the dressing, wherein the controller is communicatively coupled to the negative-pressure source to provide negative-pressure therapy.

41. The method of claim 39, wherein placing the dressing comprises:
   positioning a tissue interface adjacent to the tissue site; and
   positioning a cover over the tissue interface to form a sealed space.

42. The method of claim 41, wherein the tissue interface comprises a manifold.

43. The method of claim 35, wherein the method further comprises:
   receiving a signal of a light intensity from the light sensor;

comparing the light intensity to a light threshold;
if the light intensity is not greater than the light threshold, operating a hold loop; and
if the light intensity is greater than the light threshold, operating an activity loop.

44. The method of claim 43, wherein the hold loop comprises:
starting a timer;
comparing a current time to a hold period; and
if the current time is not greater than the hold period, holding for a predetermined time period.

45. The method of claim 44, wherein the activity loop comprises:
receiving an activity signal from the motion sensor, the activity signal indicative of a current activity;
comparing the current activity to an activity threshold;
if the current activity is greater than the activity threshold, operating an alert loop; and
if the current activity is not greater than the activity threshold, providing a prompt to engage in prescribed activity.

46. The method of claim 45, wherein the alert loop comprises:
increasing an activity counter by 1;
comparing the activity counter to a prescribed number of activity periods; and
if a completed number of activity periods indicated by the activity counter is greater than the prescribed number of activity periods, providing an alert.

47. A method for providing negative-pressure therapy, the method comprising:
providing a therapy system having:
a light sensor;
a motion sensor;
a controller communicatively coupled to the light sensor and the motion sensor, the controller configured to receive light input from the light sensor and activity input from the motion sensor, and adjust operating parameters of the negative-pressure therapy in response to the light input and the activity input;
coupling the motion sensor to a patient;
receiving a prescribed number of activity periods;
monitoring signals received from the light sensor and the motion sensor; and
in response to the signals received from the light sensor and the motion sensor, determining whether to enter a sleep mode;
if the sleep mode is entered, adjusting operating parameters of the negative-pressure therapy to operate in a sleep mode; and
if the sleep mode is not entered, adjusting operating parameters of the negative-pressure therapy to operate in a normal mode.

48. The method of claim 47, wherein the light sensor is a photosensor.

49. The method of claim 47, wherein the light sensor is a camera.

50. The method of claim 47, wherein the motion sensor is an accelerometer.

51. The method of claim 47, wherein the method further comprises positioning a dressing adjacent to a tissue site.

52. The method of claim 51, wherein the method further comprises fluidly coupling a negative-pressure source to the dressing, wherein the controller is communicatively coupled to the negative-pressure source to provide negative-pressure therapy.

53. The method of claim 51, wherein positioning the dressing comprises:
positioning a tissue interface adjacent to the tissue site; and
positioning a cover over the tissue interface to form a sealed space.

54. The method of claim 53, wherein the tissue interface comprises a manifold.

55. The method of claim 47, wherein operating in a sleep mode comprises:
setting a therapy pressure to a sleep therapy pressure;
setting an operating volume to a sleep operating volume; and
setting an operating lighting to a sleep operating lighting.

56. The method of claim 55, wherein the sleep therapy pressure is about 75 mm Hg.

57. The method of claim 55, wherein the sleep operating volume is about one-half a normal operating volume.

58. The method of claim 55, wherein a sleep operating lighting is about one-half of the normal operating lighting.

59. An apparatus for managing therapeutic activity of a patient, the apparatus comprising:
a light sensor configured to provide a light signal indicative of ambient light;
an activity sensor configured to provide an activity signal indicative of the patient's activity; and
a controller coupled to the light sensor and to the activity sensor, the controller configured to:
compare the light signal to a light threshold,
compare the activity signal to an activity threshold,
determine a number of activity intervals based on the activity signal,
prompt the patient to increase activity if the light signal is greater than the light threshold, the activity signal is less than the activity threshold, and the number of activity intervals is less than a target number.

60. The apparatus of claim 59, wherein the controller is further configured to modify an operating parameter based on the light signal and the activity signal.

61. The apparatus of claim 59, wherein the controller is further configured to modify an operating parameter if the light signal is less than the light threshold or the activity signal is less than the activity threshold.

62. The apparatus of claim 59, wherein the controller is further configured to modify an operating parameter if the light signal is less than the light threshold and the activity signal is less than the activity threshold.

63. An apparatus for providing negative-pressure therapy, the apparatus comprising:
a negative-pressure source;
a light sensor configured to provide a light signal indicative of ambient light;
an activity sensor configured to provide an activity signal indicative of the patient's activity; and
a controller coupled to the negative-pressure source, to the light sensor, and to the activity sensor, the controller configured to:
compare the light signal to a light threshold,
compare the activity signal to an activity threshold, and
modify an operating parameter if the light signal is less than the light threshold and the activity signal is less than the activity threshold.

64. The apparatus of claim 63, wherein the operating parameter is an alarm threshold.

65. The apparatus of claim 63, wherein the operating parameter is a therapy pressure of the negative-pressure source.

66. A method for providing negative-pressure therapy, the method comprising:
provide a therapy system having:
a light sensor;
a motion sensor;
a user interface;
a controller communicatively coupled to the light sensor and the motion sensor, the controller configured to receive light input from the light sensor and activity input from the motion sensor, and adjust operating parameters of the negative-pressure therapy in response to the light input and the activity input;
setting one of an active mode and a sleep mode of the therapy system with the user interface;
monitoring signals received from the light sensor and the motion sensor; and
in response to the signals received from the light sensor and the motion sensor, determining whether to enter the sleep mode;
if the sleep mode is entered, adjusting operating parameters of negative-pressure therapy to operate in the sleep mode; and
if the sleep mode is not entered, adjusting operating parameter of negative-pressure therapy to operate in the active mode.

67. A method for providing negative-pressure therapy, the method comprising:
providing a therapy system having:
a light sensor;
a motion sensor;
a user interface;
a controller communicatively coupled to the light sensor and the motion sensor, the controller configured to receive light input from the light sensor and activity input from the motion sensor, and adjust operating parameters of the negative-pressure therapy in response to the light input and the activity input;
setting one of an active mode and a sleep mode of the therapy system with the user interface;
monitoring signals received from the light sensor and the motion sensor; and
transmitting the signals received from the light sensor and the motion sensor to a remote server.

* * * * *